(12) United States Patent
Kwon

(10) Patent No.: US 8,562,544 B2
(45) Date of Patent: Oct. 22, 2013

(54) PEN TYPE DEVICE FOR ULTRASOUND GUIDED FINE NEEDLE ASPIRATION CYTOLOGY AND BIOPSY

(75) Inventor: Hyuk Ho Kwon, Uiwang-si (KR)

(73) Assignee: Soon Won Kwon, Fullerton, CA (US)

( * ) Notice: Subject to any disclaimer, the term of this patent is extended or adjusted under 35 U.S.C. 154(b) by 0 days.

(21) Appl. No.: 13/360,100

(22) Filed: Jan. 27, 2012

(65) Prior Publication Data

US 2013/0172777 A1 Jul. 4, 2013

(30) Foreign Application Priority Data

Jan. 3, 2012 (KR) ..................... 10-2012-0000533

(51) Int. Cl.
*A61B 10/00* (2006.01)
*A61M 5/00* (2006.01)
*A61M 37/00* (2006.01)

(52) U.S. Cl.
USPC ........... 600/565; 600/562; 600/563; 600/564; 600/566; 600/567; 604/117; 604/131; 604/207; 604/208; 604/209; 604/210; 604/211

(58) Field of Classification Search
USPC .......... 600/562–567; 604/117, 131, 207–211
See application file for complete search history.

(56) References Cited

U.S. PATENT DOCUMENTS

| 5,374,252 A * | 12/1994 | Banks et al. ................. 604/158 |
| 5,425,376 A * | 6/1995 | Banys et al. ................. 600/566 |
| 6,203,529 B1 * | 3/2001 | Gabriel et al. ............... 604/192 |
| 6,283,925 B1 * | 9/2001 | Terwilliger .................. 600/568 |
| 2006/0229562 A1 | 10/2006 | Marsh et al. |
| 2006/0229570 A1 | 10/2006 | Lovell et al. |
| 2009/0326412 A1 * | 12/2009 | Pakter ........................... 600/567 |
| 2011/0152716 A1 * | 6/2011 | Chudzik et al. ............... 600/567 |

FOREIGN PATENT DOCUMENTS

| KR | 20050032018 | 4/2005 |
| KR | 20110086543 | 7/2011 |

* cited by examiner

*Primary Examiner* — Sean Dougherty
*Assistant Examiner* — Devin Henson
(74) *Attorney, Agent, or Firm* — IPLA P.A.; James E. Bame

(57) ABSTRACT

A pen type device for ultrasound guided fine needle aspiration cytology and biopsy comprises a hollow body having a needle hole, a sliding part slidably mounted inside the body, elastic members mounted inside the body, a syringe having a cylinder mounted, a rotating part disposed inside the sliding part and the body, a head screw-coupled to the rear end of the sliding part and drawn out from the body, and a negative pressure generating part mounted on the body to generate negative pressure to the syringe by pulling a piston of the syringe when a button located on the outer face of the body is pushed.

13 Claims, 6 Drawing Sheets

PEN TYPE DEVICE FOR ULTRASOUND GUIDED FINE NEEDLE ASPIRATION CYTOLOGY AND BIOPSY

CROSS REFERENCES

Applicant claims foreign priority under Paris Convention to Korean Patent Application No. 10-2012-0000533 filed Jan. 3, 2012, with the Korean Intellectual Property Office, where the entire contents are incorporated herein by reference.

BACKGROUND OF THE INVENTION

1. Field of the Invention

The present invention relates to a pen type device for ultrasound guided fine needle aspiration cytology and biopsy, and more particularly, to a pen type device for ultrasound guided fine needle aspiration cytology and biopsy, which is easy to manipulate and carry and allows a doctor to correctly extract cells or tissues from the lesion.

2. Background of the Invention

In general, when a patient has a tumor or a nodule in his or her body, biopsy or cytology must be essentially took in order to rapidly judge whether or not the tumor or the nodule is malignant and set a way for treating the tumor or the nodule. Particularly, in the case that a doctor distinguishes a tumor grown around an area, which is not deep from the skin, such as lymph nodes, muscles, thyroid, breasts, or others, in order to minimize the patient's burden and adopt an effective curing method, the doctor extracts and examines cells or tissues by the least invasive method using a fine needle.

In this instance, in the case of a tumor which is seen with naked eyes or easily touched with the hands, the doctor can carry out biopsy by inserting a biopsy needle into a suspected tumor without using ultrasonic waves. However, on the contrary, in the case of a tumor which is not seen with naked eyes or not touched with the hands because the tumor is small or grows in a deeper place, the doctor carries out cytology or biopsy while looking at a monitor using an ultrasound medical instrument, so that the doctor can easily and correctly extract cells or tissues by inserting the biopsy needle into the lesion.

For this, general syringes have been widely used, but the doctor often repeats the examination in order to obtain correct results because such syringes are not easy to manipulate and are deteriorated in cell extraction rate. Moreover, conventional ultrasound guided devices for biopsy have several problems in that they are not easy to manipulate and carry, in that it is difficult to correctly extract cells or tissues of the lesion, and in that they are not widely used because they have no special advantages in comparison with general syringes.

SUMMARY OF THE INVENTION

Accordingly, the present invention has been made to solve the above-mentioned problems occurring in the prior arts, and it is an object of the present invention to provide a pen type device for ultrasound guided fine needle aspiration cytology and biopsy, which is easy to manipulate and carry and allows a doctor to correctly extract cells or tissues from the lesion.

The above and other objects, features and advantages of the present invention will be apparent from the following detailed description of the preferred embodiments of the invention in conjunction with the accompanying drawings.

To accomplish the above object, according to the present invention, there is provided a pen type device for ultrasound guided fine needle aspiration cytology and biopsy including: a hollow body having a needle hole formed at the front end thereof, the body being hollow at the rear end; a sliding part slidably mounted inside the body; elastic members mounted around the sliding part and inside the body to provide elasticity to return the sliding part backward; a syringe having a cylinder mounted at the front end of the sliding part and a needle drawn out from or inserted into the needle hole by a back-and-forth movement of the sliding part; a rotating part disposed at a front end of the sliding part and inside the body to rotate the syringe when the sliding part moves back and forth; a head screw-coupled to the rear end of the sliding part and drawn out from the body to control a movement distance of the sliding part according to the length that the head is screw-coupled with the sliding part; and a negative pressure generating part mounted on the body to generate negative pressure to the syringe by pulling a piston of the syringe when a button located on the outer face of the body is pushed.

The body comprises an indicator formed on a side portion of the rear end thereof, and the head comprises an indication portion disposed on a side portion thereof to indicate the movement distance of the sliding part by being exposed through the indicator.

The head has a diameter or a width larger than an inner diameter of the body so that the head is caught to the rear end of the body.

The pen type device for ultrasound guided fine needle aspiration cytology and biopsy further includes: a rotary knock module, which is disposed inside the sliding part and the body, which makes the sliding part move backward and be caught by elasticity of the elastic members when a user presses the head and releases the head in a state where the sliding part is moved forward so that the needle keeps the projected state from the body, and which makes the sliding part move backward by being released when the user presses and releases the head again so that the needle is inserted into the body.

The rotating part includes: a screw projection rotatably mounted at the front end of the sliding part and formed along the outer circumferential surface of the rotary body that is fixed in such a way as to be rotated with the cylinder of the syringe; and a rotation guiding projection that is formed on the inner face of the body and joined to the screw projection, and guides the rotary body by the back-and-forth movement of the sliding part in such a way as to be rotated with the syringe.

The rotating part is rotatably joined to the outer face of the body and further includes a guide projection formed on the inner face of the rotating part so as to be joined to the screw projection; and a rotational ring for guiding the back-and-forth movement of the rotary body according to a rotational direction.

The rotating part further includes a straight line portion formed on the front side of the screw projection to control the rotation of the rotary body within a predetermined distance at the early stage that the sliding part advances forward.

The rotation guiding projections are a plurality of balls rotatably mounted along the inner circumferential surface of the body.

The negative pressure generating part includes: a pulley rotatably mounted in the body; a wire connected to a hand grip of the piston and wound on the pulley; a gear disposed at one side of the pulley; and a return spring adapted to provide elasticity to the button so that the button is spaced apart from the gear, the button being exposedly mounted on the body to make the gear rotate when the button is pushed.

The body includes a cap which is separable at the front end and is made of a transparent material.

The pen type device for ultrasound guided fine needle aspiration cytology and biopsy further includes a cover detachably mounted on the outer face of the front end of the body.

As described above, the pen type device for ultrasound guided fine needle aspiration cytology and biopsy according to the present invention is easy to manipulate and carry and allows a doctor to correctly extract cells or tissues around the lesion.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
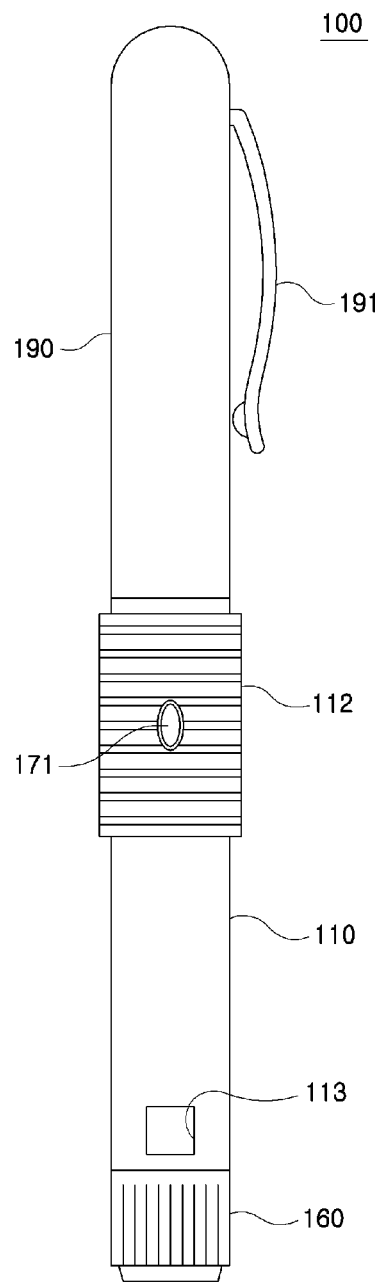
FIG. 1 is a front view of a pen type device for ultrasound guided fine needle aspiration cytology and biopsy according to a preferred embodiment of the present invention.

While example embodiment of the present invention is capable of various modifications and alternative forms, specific embodiments of the present invention are shown by way of example in the drawings and will herein be described in detail. It should be understood, however, that there is no intent to limit the example embodiment of the present invention to the particular forms disclosed, but on the contrary, the example embodiment of the invention is to cover all modifications, equivalents, and alternatives falling within the scope of the present invention.

Hereinafter, reference will be now made in detail to the preferred embodiment of the present invention with reference to the attached drawings. Similar or corresponding components have the same reference numerals without regard to drawing numbers, and repeated description on the components will be omitted.

Figure 2:
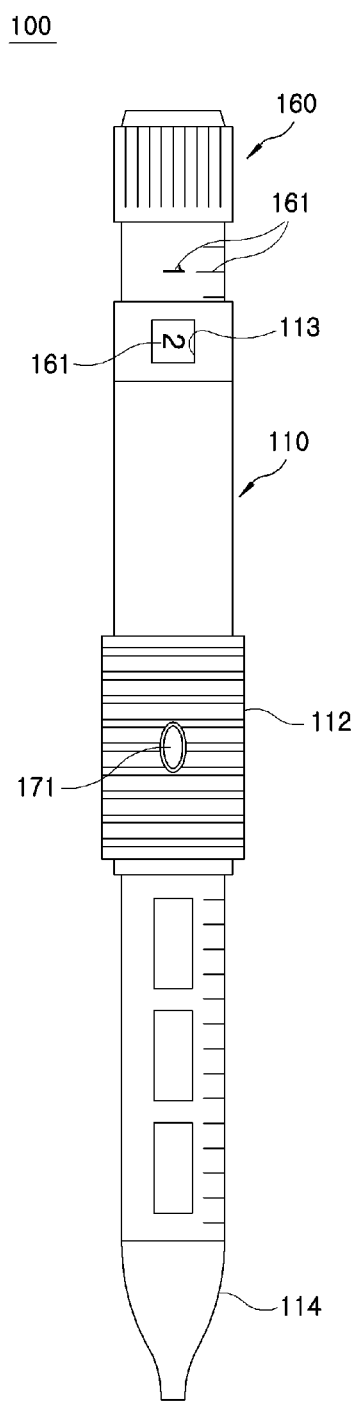
FIG. 2 is a front view of a pen type device for ultrasound guided fine needle aspiration cytology and biopsy according to a modification of the present invention.
Figure 3:
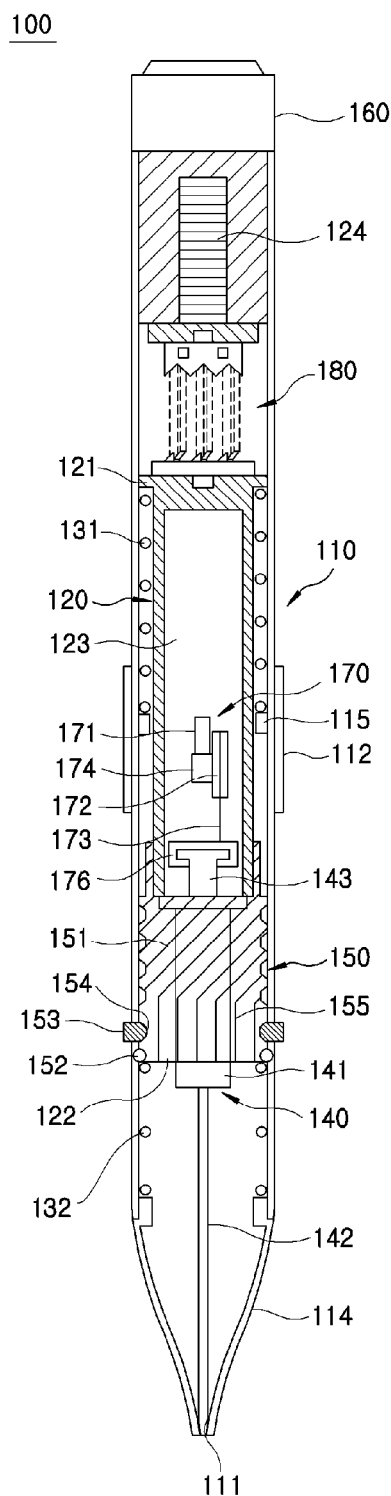
FIG. 3 is a side sectional view of the pen type device for ultrasound guided fine needle aspiration cytology and biopsy according to the present invention.

FIG. 1 is a front view of a pen type device for ultrasound guided fine needle aspiration cytology and biopsy according to a preferred embodiment of the present invention, FIG. 2 is a front view of a pen type device for ultrasound guided fine needle aspiration cytology and biopsy according to a modification of the present invention, and FIG. 3 is a side sectional view of the pen type device for ultrasound guided fine needle aspiration cytology and biopsy according to the present invention.

As shown in FIGS. 1 to 3, the pen type device 100 for ultrasound guided fine needle aspiration cytology and biopsy according to the present invention includes a body 110, a sliding part 120, elastic members 131 and 132, a syringe 140, a rotating part 150, a head 160, and a negative pressure generating part 170.

The body 110 is in a hollow form and includes a needle hole 111 formed at the front end thereof. The body 110 is opened at the rear end thereof, and has a hand grip portion 112 formed on the outer circumferential surface of the central portion thereof and made of a rubber material to allow a user to easily grip.

The body 110 further includes an indicator 113 formed on a side of the rear end thereof and a separable cap 114 detachably mounted at the front end and made of a transparent material. Here, the cap 114 may be screw-coupled to the front end of the body 110, and may be replaced with a disposable aseptic product for sanitation. Moreover, because the cap 114 is made of the transparent material, the user can see the syringe 140 disposed inside the body 110.

A separable cover 190 may be mounted on the outer face of the front end of the body 110. Here, the cover 190 opens and closes the needle hole 111 formed in the front end of the body 110, and may have a clip 191 for allowing the user to hang it on a pocket or the likes.

The sliding part 120 includes: a flange 121 for supporting the elastic member 30 slidably mounted around the sliding part 120 and on the inner face of the body 110; a groove 123 formed in a longitudinal direction to prevent interference with the rotating part 150 during sliding; and a screw-coupling portion 124 disposed at the rear end for screw-coupling with the head 160.

The elastic members 131 and 132, as an example, may be a single coil spring, or like this embodiment, may be constituted of a first coil spring 131 and a second coil spring 132. Here, the first spring 131 is mounted on a support protrusion 115 inside the body 110 to provide the flange 121 of the sliding part 120 with elasticity, so that the sliding part 120 is returned backward. Furthermore, the second spring 132 is mounted to support the front end of a rotary body 122 at the front side in the body 110 to thereby provide the rotary body 122 with elasticity, so that the rotary body 122 of the sliding part 120 is returned backward.

The syringe 140 is to extract cells or tissues of the lesion, and includes: a cylinder 141 mounted at the front end of the sliding part 120; and a needle 142 that is drawn out from or inserted into the needle hole 111 according to a back-and-forth movement of the sliding part 120.

Length and shape of the needle 142 may be selected according to the lesions. For instance, the needle 142 may be painted or indicated with paint in between in such a way as to be seen well by ultrasonic waves. Moreover, the needle 142 can enhance a tissue extraction rate when the needle 142 has a widened opening and is rotated in a state side wings are sharpened. Alternatively, an edge portion of the needle 142 may be formed in a screw shape and may have a plurality of tiny projections.

The rotating part 150 is disposed at a front end of the sliding part 20 and inside the body 110 in order to rotate the syringe 140 when the sliding part 120 moves back and forth. For an example, the rotating part 150 may be a ring bearing, or like this embodiment, includes: a screw projection 151 rotatably mounted at the front end of the sliding part 120 and formed along the outer circumferential surface of the rotary body 122 that is fixed in such a way as to be rotated with the cylinder 141 of the syringe 140; and a rotation guiding projection 152 that is formed on the inner face of the body 110, joined to the screw projection 151, and guides the rotary body 122 by the back-and-forth movement of the sliding part 120 in such a way as to be rotated with the syringe 140. In the meantime, the rotary body 122 is detachably joined to the remaining portion of the sliding part 120 by a forcedly fitting method, so that the syringe 140 can be detachably mounted.

The rotating part 150 is rotatably joined to the outer face of the body 110 and may further include: a guide projection 154 formed on the inner face of the rotating part 150 so as to be joined to the screw projection 151; and a rotational ring 153 for guiding the back-and-forth movement of the rotary body 122 according to a rotational direction. Furthermore, the rotating part 150 may further include a straight line portion 155 formed on the front side of the screw projection 151 to control the rotation of the rotary body 122 within a predetermined distance at the early stage that the sliding part 120 advances. For instance, the screw projection 151 may be 10 mm in length and the straight line portion 155 may be also 10 mm in length. Accordingly, the projection length of the needle 142 due to the advance of the syringe 140 may be 20 mm.

A plurality of the rotation guiding projections 152 may be rotatably mounted along the inner circumferential surface of the body 110, and in this instance, each of the rotation guiding projections 152 may be a ball.

The head 160 is screw-coupled to the rear end of the sliding part 120 and drawn out from the body 110, and can control a movement distance of the sliding part 120 according to the length that the head 160 is screw-coupled with the sliding part 120, and includes an indication portion 161 disposed on a side thereof to indicate the movement distance of the sliding part 120 by being exposed through the indicator 113. As an example, the indication portion 161 may include gradations and numbers.

The head 160 may have a diameter or a width larger than an inner diameter of the body 110, so that the head 160 is caught to the rear end of the body 110.

Figure 4:
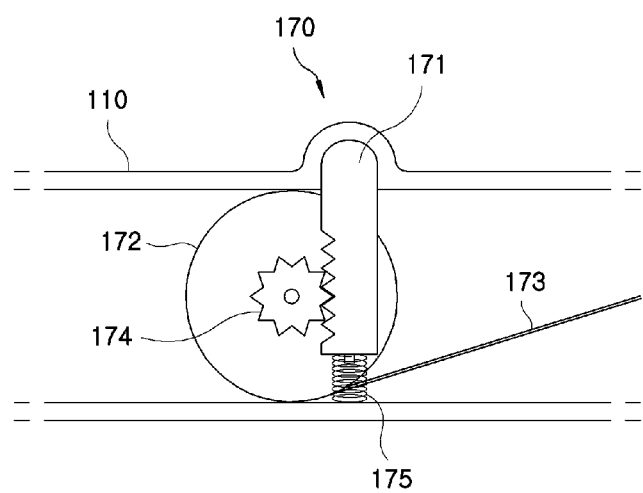
FIG. 4 is a side view of a negative pressure generating part of the pen type device for ultrasound guided fine needle aspiration cytology and biopsy according to the present invention.

The negative pressure generating part 170 is mounted on the body 110, and generates negative pressure to the syringe 140 when the user pushes a button 171 located on the outer face thereof so that a piston 143 of the syringe 140 is pulled, whereby the present invention can extract tissues or cells of the lesion. As shown in FIG. 4, as an example, the negative pressure generating part 170 includes: a pulley 172 rotatably mounted in the body 110; a wire 173 connected to a hand grip of the piston 143 and wound on the pulley 172; a gear 174 disposed at one side of the pulley 172; and a return spring 175 adapted to provide elasticity to the button 171 so that the button 171 is spaced apart from the gear 174, wherein the button 171 is exposedly mounted on the body 110 and makes the gear 174 rotate when the button 171 is pushed. Here, the wire 173 may be fixed to a fitting portion 176 whose end portion is fit to the hand grip of the piston 143.

The present invention may further include a rotary knock module 180 adapted to stop the sliding part 120 at a predetermined distance after the sliding part 120 is advanced forward, for instance, at a distance of 10 mm.

The rotary knock module 180 may adopt the operation and structure of a knock type pen. The rotary knock module 180 is disposed inside the sliding part 120 and the body 110. In this instance, when the user presses the head 160 and releases the head 160 in a state where the sliding part 120 is moved forward, the sliding part 120 is moved backward and caught by elasticity of the elastic members 131 and 132, so that the needle 142 keeps a state where the needle 142 is drawn out from the body 110. After that, when the user presses and releases the head 160 again, the sliding part 120 is moved backward by being released, so that the needle 142 is inserted into the body 110.

Figure 5:
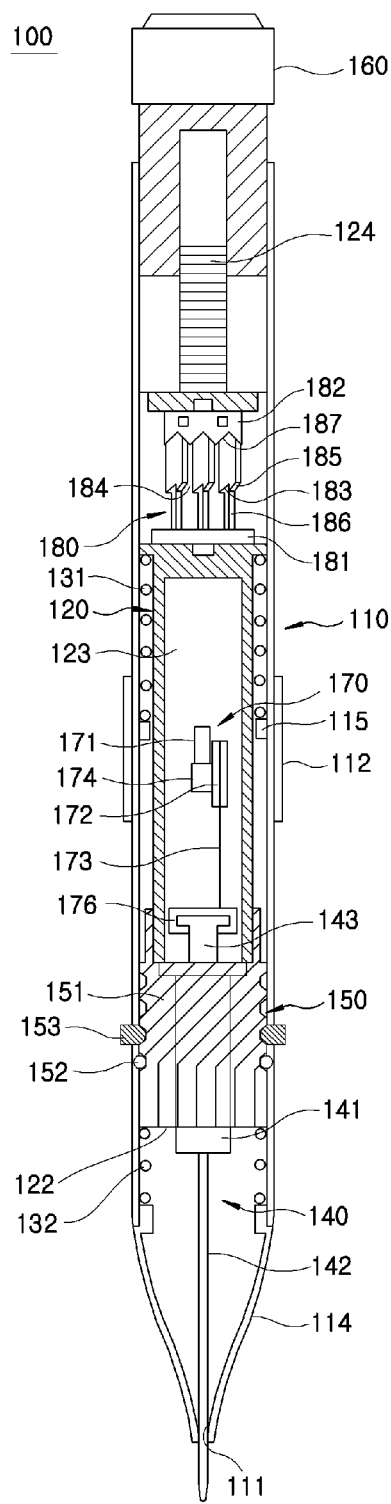
FIGS. 5 and 6 are side sectional views for explaining the operation of the pen type device for ultrasound guided fine needle aspiration cytology and biopsy according to the present invention.

As shown in FIG. 5, the rotary knock module 180 includes: a holder 181 joined to one of divided ends of the sliding part 120; a knock member 182 joined to the other of the divided ends of the sliding part 120; support protruding jaws 183 formed on the inner face of the body 110 to restrict the holder 181; a guide groove 184 formed between the support protruding jaws 183 to guide elevation of the knock member 182 and to move the sliding part 120 backward when the holder 181 is moved upward; and a rotational inclined jaw 185 formed between the guide groove 184 and the support protruding jaws 183 to rotate the holder 181 for the backward movement of the sliding part 120. Here, the rotary knock module 180 may further include: a holder key 186 formed on the upper portion of the holder 181 in such a fashion that the upper end is caught to the support protruding jaws 183 or moved to the guide groove 184; and a gear portion 187 formed at the lower end of the knock member 182 in such a way as to go down in a state where it is matched with the holder key 186. Moreover, the rotary knock module 180 and the sliding part 120 are constructed in such a way as to prevent a mutual interference in their sliding movement.

Now, the operation of the pen type device for ultrasound guided fine needle aspiration cytology and biopsy according to the present invention will be described.

As shown in FIG. 5, when the head 160 is rotated from the sliding part 120, the head 160 is drawn out from the body 110, and in this instance, the indication portion 161 (See FIG. 2) is indicated on the indicator 113 (See FIG. 2) corresponding to the rotation number of the head 160 or the movement distance of the sliding part 120. In the state where the head 160 is not pushed, as shown in FIG. 3, the needle 142 of the syringe 140 is matched to an end line of the cap 114.

When the head 160 is pushed and the sliding part 120 is advanced forward, for instance, to 10 mm, the needle 142 of the syringe 140 is projected to 10 mm from the needle hole 111. In this instance, the straight line portion 155 is guided by the rotation guiding projection 152 and the syringe 140 is advanced forward without being rotated, so that a damage of tissues is minimized before the needle 142 is inserted into the lesion. Furthermore, when the user releases the head 160, the needle 142 is stopped in the state where the needle 142 is projected to 10 mm by the rotary knock module 180. Accordingly, in the case that the user releases the head 160 in the state where the insertion of the needle 142 is stopped after the needle 142 is inserted into the lesion, the needle 142 is stopped in the projected state, and hence, the user feels less fatigue and can check the inserted state of the needle 142 into the lesion again, in the stopped state, using ultrasonic waves. In this instance, the wire 173 gets loose from the pulley 172, and the syringe 140 is advanced forward without any change in the internal pressure.

Figure 6:
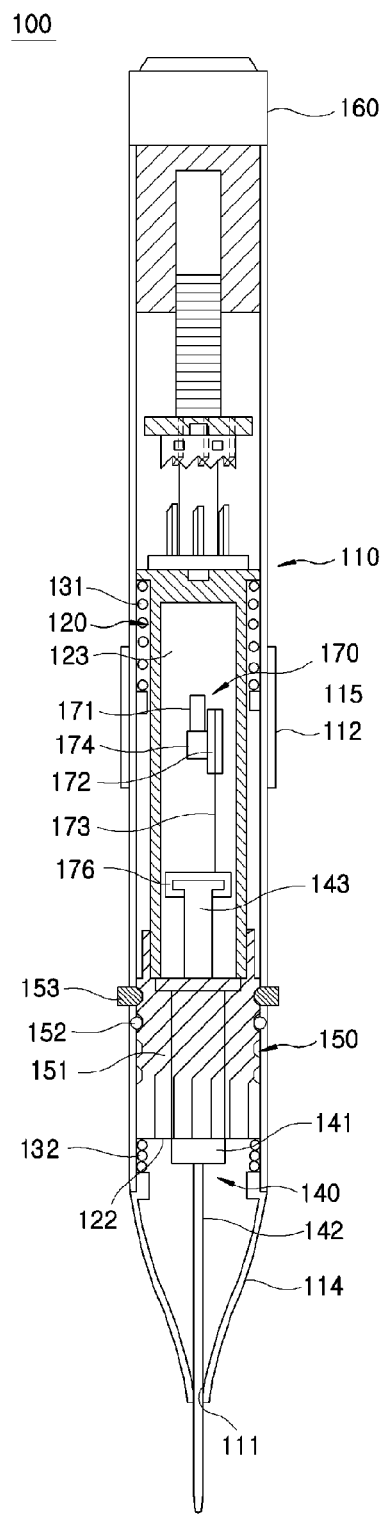

Additionally, as shown in FIG. 6, when the head 160 is pressed and advanced further to 10 mm, the end of the needle 142 is correctly inserted into the lesion, and the rotary body 122 is rotated together with the syringe 140 by the screw projection 151 and the rotation guiding projection 152. Accordingly, the needle 142 can extract cells or tissues in the lesion to the maximum. After that, when the user pushes the button 171 with the third or fourth finger to move the piston 143 backward, negative pressure is applied to the syringe 140, and the cells or tissues of the lesion can be extracted by the negative pressure of the syringe 140.

In the meantime, if the negative pressure is continuously applied to the syringe 140, too much blood is inhaled, and hence, it prevents examination of the cells. Accordingly, when the user releases the button 171 in order to minimize inhalation of blood and to make the device be operated only in case of necessity, the pulley 172 is returned to the original position by elasticity of the return spring 175 (See FIG. 4).

While the present invention has been particularly shown and described with reference to exemplary embodiment thereof, it will be understood by those of ordinary skill in the art that various changes in form and details may be made therein without departing from the spirit and scope of the present invention as defined by the following claims.

What is claimed is:

1. A pen type device for ultrasound guided fine needle aspiration cytology and biopsy comprising:
    a hollow body having a needle hole formed at the front end thereof, the body being hollow at the rear end;
    a sliding part slidably mounted inside the body;
    elastic members mounted around the sliding part and inside the body to provide elasticity to return the sliding part backward;
    a syringe having a cylinder mounted at the front end of the sliding part and a needle drawn out from or inserted into the needle hole by a back-and-forth movement of the sliding part;
    a rotating part disposed at a front end of the sliding part and inside the body to rotate the syringe when the sliding part moves back and forth;
    a head screw-coupled to the rear end of the sliding part and drawn out from the body to control a movement distance of the sliding part according to the length that the head is screw-coupled with the sliding part; and
    a negative pressure generating part mounted on the body to generate negative pressure to the syringe by pulling a piston of the syringe when a button located on the outer face of the body is pushed.

2. The pen type device according to claim 1, wherein the body comprises an indicator formed on a side portion of the rear end thereof, and
    wherein the head comprises an indication portion disposed on a side portion thereof to indicate the movement distance of the sliding part by being exposed through the indicator.

3. The pen type device according to claim 1, wherein the head has a diameter or a width larger than an inner diameter of the body so that the head is caught to the rear end of the body.

4. The pen type device according to claim 1, further comprising:
    a rotary knock module, which is disposed inside the sliding part and the body, which makes the sliding part move backward and be caught by elasticity of the elastic members when a user presses the head and releases the head in a state where the sliding part is moved forward so that the needle keeps the projected state from the body, and which makes the sliding part move backward by being released when the user presses and releases the head again so that the needle is inserted into the body.

5. The pen type device according to claim 1, wherein the rotating part comprises:
    a screw projection rotatably mounted at the front end of the sliding part and formed along an outer circumferential surface of a rotary body that is fixed in such a way as to be rotated with the cylinder of the syringe; and
    a rotation guiding projection that is formed on the inner face of the body and joined to the screw projection, and guides the rotary body by the back-and-forth movement of the sliding part in such a way as to be rotated with the syringe.

6. The pen type device according to claim 5, wherein the rotating part that is rotatably joined to the outer face of the body further comprises:
    a guide projection formed on the inner face of the rotating part so as to be joined to the screw projection; and a rotational ring for guiding the back-and-forth movement of the rotary body according to a rotational direction.

7. The pen type device according to claim 6, wherein the rotating part further comprises:
    a straight line portion formed on the front side of the screw projection to control the rotation of the rotary body within a predetermined distance at an early stage that the sliding part advances forward.

8. The pen type device according to claim 5, wherein the rotating part further comprises: a straight line portion formed on the front side of the screw projection to control the rotation of the rotary body within a predetermined distance at an early stage that the sliding part advances forward.

9. The pen type device according to claim 5, wherein the rotation guiding projection is a ball rotatably mounted along the inner circumferential surface of the body.

10. The pen type device according to claim 1, wherein the negative pressure generating part comprises:
    a pulley rotatably mounted in the body;
    a wire connected to a hand grip of the piston and wound on the pulley;
    a gear disposed at one side of the pulley; and
    a return spring adapted to provide elasticity to the button so that the button is spaced apart from the gear, the button being exposedly mounted on the body to make the gear rotate when the button is pushed.

11. The pen type device according to claim 1, wherein the body comprises: a cap which is separable at the front end of the body and is made of a transparent material.

12. The pen type device according to claim 11, further comprising: a cover detachably mounted on the outer face of the front end of the body.

13. The pen type device according to claim 1, further comprising: a cover detachably mounted on the outer face of the front end of the body.

* * * * *